United States Patent
Gehrke et al.

(10) Patent No.: US 11,419,553 B2
(45) Date of Patent: Aug. 23, 2022

(54) SLEEPING OR RECLINING FURNITURE, ANALYZING UNIT FOR A SENSOR OF SLEEPING OR RECLINING FURNITURE, AND METHOD FOR ANALYZING SIGNALS OF A SENSOR

(71) Applicant: DEWERTOKIN GMBH, Kirchlengern (DE)

(72) Inventors: Karsten Gehrke, Porta Westfalica (DE); Armin Hille, Bielefeld (DE); Steffen Loley, Osnabrück (DE); Alexander Tews, Bielefeld (DE)

(73) Assignee: Dewertokin Technology Group Co., Ltd, Jiaxing (CN)

( * ) Notice: Subject to any disclaimer, the term of this patent is extended or adjusted under 35 U.S.C. 154(b) by 1001 days.

(21) Appl. No.: 16/067,487

(22) PCT Filed: Dec. 30, 2016

(86) PCT No.: PCT/EP2016/082919
§ 371 (c)(1),
(2) Date: Jun. 29, 2018

(87) PCT Pub. No.: WO2017/114948
PCT Pub. Date: Jul. 6, 2017

(65) Prior Publication Data
US 2019/0021675 A1 Jan. 24, 2019

(30) Foreign Application Priority Data

Dec. 30, 2015 (DE) ...................... 20 2015 107 148.5
May 24, 2016 (DE) ...................... 10 2016 109 524.9
Oct. 7, 2016 (DE) ...................... 20 2016 105 634.9

(51) Int. Cl.
*A61B 5/0205* (2006.01)
*A47C 31/00* (2006.01)
(Continued)

(52) U.S. Cl.
CPC .......... *A61B 5/6892* (2013.01); *A47C 17/162* (2013.01); *A47C 17/163* (2013.01);
(Continued)

(58) Field of Classification Search
CPC ...... A61G 7/015; A61G 7/018; A61G 7/0524; A61G 7/1065; A61G 7/1063; A61G 7/16;
(Continued)

(56) References Cited

U.S. PATENT DOCUMENTS 7,699,784 B2 * 4/2010 Wan Fong ......... A61B 5/02444
600/481
8,981,679 B2 3/2015 Hille
(Continued)

FOREIGN PATENT DOCUMENTS

CN 1741782 A 3/2006
CN 1980602 A 6/2007
(Continued)

OTHER PUBLICATIONS

Chinese Search Report dated Mar. 26, 2020 with respect to counterpart Chinese patent application 201680079659.8.
(Continued)

*Primary Examiner* — Robert G Santos
(74) *Attorney, Agent, or Firm* — Henry M. Feiereisen LLC

(57) ABSTRACT

The invention relates to an analyzing unit (9') for connecting to at least one sensor (12) which can be coupled to sleeping or reclining furniture in order to detect vibrations, movement, and/or sound. The analyzing unit (9') is designed to process and analyze the signals of the at least one sensor (12) and detect physiological parameters (P) of a person using the sleeping or reclining furniture, and the analyzing unit (9') is designed to transmit data to or exchange data with at least one external component. The invention further relates to a
(Continued)

method for analyzing signals of at least one such sensor (12) and to sleeping or reclining furniture, in particular a bed (1), comprising at least one such sensor (12).

24 Claims, 8 Drawing Sheets

(51) Int. Cl.
| | | |
|---|---|---|
| A61G 7/05 | (2006.01) | |
| A61G 7/015 | (2006.01) | |
| A61G 7/018 | (2006.01) | |
| A61G 13/02 | (2006.01) | |
| A61G 13/08 | (2006.01) | |
| A61B 5/00 | (2006.01) | |
| A47C 21/00 | (2006.01) | |
| A61B 5/113 | (2006.01) | |
| A47C 27/00 | (2006.01) | |
| A61G 7/075 | (2006.01) | |
| A61G 7/10 | (2006.01) | |
| A61G 7/16 | (2006.01) | |
| A47C 20/04 | (2006.01) | |
| A47C 17/16 | (2006.01) | |
| A47C 19/02 | (2006.01) | |
| A61B 5/11 | (2006.01) | |
| G05B 19/416 | (2006.01) | |
| A61B 5/024 | (2006.01) | |
| A61B 5/08 | (2006.01) | |

(52) U.S. Cl.
CPC .......... *A47C 19/027* (2013.01); *A47C 20/041* (2013.01); *A47C 21/003* (2013.01); *A47C 27/00* (2013.01); *A47C 31/00* (2013.01); *A47C 31/008* (2013.01); *A61B 5/002* (2013.01); *A61B 5/0022* (2013.01); *A61B 5/0205* (2013.01); *A61B 5/113* (2013.01); *A61B 5/1116* (2013.01); *A61B 5/1123* (2013.01); *A61B 5/1135* (2013.01); *A61B 5/4806* (2013.01); *A61B 5/4809* (2013.01); *A61B 5/6891* (2013.01); *A61B 5/725* (2013.01); *A61B 5/746* (2013.01); *A61G 7/015* (2013.01); *A61G 7/018* (2013.01); *A61G 7/0506* (2013.01); *A61G 7/0524* (2016.11); *A61G 7/0755* (2013.01); *A61G 7/1065* (2013.01); *A61G 7/16* (2013.01); *A61G 13/02* (2013.01); *A61G 13/08* (2013.01); *G05B 19/416* (2013.01); *A61B 5/024* (2013.01); *A61B 5/02444* (2013.01); *A61B 5/0816* (2013.01); *A61G 2200/327* (2013.01); *A61G 2200/34* (2013.01); *G05B 2219/43196* (2013.01)

(58) Field of Classification Search
CPC ...... A61G 13/02; A61G 13/08; A47C 17/162; A47C 17/163; A47C 20/041; A47C 20/04; A47C 20/08; A47C 21/003; A47C 31/008; A61B 5/6892; A61B 5/6891; A61B 5/002; A61B 5/0022; A61B 5/0205; A61B 5/1116; A61B 5/1123; A61B 5/113; A61B 5/1135; A61B 5/4806; A61B 5/4809; A61B 5/725; A61B 5/746; G05B 19/416
USPC ............................................ 5/616, 613, 600
See application file for complete search history.

(56) References Cited

U.S. PATENT DOCUMENTS

| | | | |
|---|---|---|---|
| 9,230,764 B2 | 1/2016 | Hille | |
| 9,236,822 B2 | 1/2016 | Hille et al. | |
| 9,252,692 B2 | 2/2016 | Hille | |
| 9,330,561 B2* | 5/2016 | Proud | A61B 5/1118 |
| 9,331,610 B2 | 5/2016 | Hille | |
| 9,478,122 B2 | 10/2016 | Hille | |
| 9,591,995 B2* | 3/2017 | Blumberg | A47C 17/62 |
| 9,713,387 B2 | 7/2017 | Hille | |
| 9,715,822 B2 | 7/2017 | Hille | |
| 9,792,810 B2 | 10/2017 | Hille et al. | |
| 9,836,034 B2* | 12/2017 | Hille | G05B 15/02 |
| 10,357,413 B2* | 7/2019 | Buerstner | A61G 13/08 |
| 10,448,749 B2* | 10/2019 | Palashewski | G05B 15/02 |
| 10,729,357 B2* | 8/2020 | Larson | A61B 5/6801 |
| 2008/0005838 A1* | 1/2008 | Wan Fong | A61B 5/4094 |
| | | | 5/600 |
| 2008/0052837 A1* | 3/2008 | Blumberg | A47C 17/04 |
| | | | 5/727 |
| 2010/0101022 A1 | 4/2010 | Riley et al. | |
| 2011/0037425 A1 | 2/2011 | Gehrke et al. | |
| 2011/0263950 A1* | 10/2011 | Larson | A61B 5/026 |
| | | | 600/301 |
| 2012/0253142 A1 | 10/2012 | Mecar et al. | |
| 2014/0249825 A1* | 9/2014 | Proud | H02J 50/80 |
| | | | 704/275 |
| 2014/0266733 A1 | 9/2014 | Hayes et al. | |
| 2014/0335490 A1* | 11/2014 | Baarman | A61B 5/1118 |
| | | | 434/236 |
| 2015/0019020 A1* | 1/2015 | Hille | G05B 15/02 |
| | | | 700/275 |
| 2015/0025688 A1 | 1/2015 | Hille et al. | |
| 2015/0026890 A1 | 1/2015 | Hille et al. | |
| 2015/0035457 A1 | 2/2015 | Hille et al. | |
| 2015/0199484 A1 | 7/2015 | Morris et al. | |
| 2015/0241857 A1 | 8/2015 | Hille | |
| 2016/0081866 A1 | 3/2016 | Hille | |
| 2016/0089287 A1* | 3/2016 | Buerstner | A61G 13/105 |
| | | | 5/616 |
| 2016/0100696 A1* | 4/2016 | Palashewski | A61B 5/6892 |
| | | | 700/90 |
| 2016/0377273 A1 | 12/2016 | Hille | |
| 2019/0008283 A1* | 1/2019 | Gehrke | A47C 17/163 |
| 2019/0008284 A1* | 1/2019 | Gehrke | A61B 5/0205 |
| 2019/0021675 A1* | 1/2019 | Gehrke | A47C 21/003 |
| 2019/0357696 A1* | 11/2019 | Palashewski | G05B 15/02 |
| 2020/0383854 A1* | 12/2020 | Gehrke | A47C 31/00 |

FOREIGN PATENT DOCUMENTS

| | | | | |
|---|---|---|---|---|
| CN | 101467881 A | 7/2009 | | |
| CN | 101960797 A | 1/2011 | | |
| CN | 103284690 A | 9/2013 | | |
| CN | 103780691 A | 5/2014 | | |
| CN | 104257159 A | 1/2015 | | |
| CN | 204306471 U | 5/2015 | | |
| DE | 202016105634 U1 * | 5/2017 | ........... | A47C 17/162 |
| JP | 2004-344675 | 12/2004 | | |
| JP | 2004344675 A | 12/2004 | | |
| JP | 2005177471 A | 7/2005 | | |
| JP | JP 2005253957 A | 9/2005 | | |
| WO | WO 0164103 A1 | 9/2001 | | |
| WO | WO-2013086363 A2 * | 6/2013 | ........... | A61B 5/002 |
| WO | WO 2013/173640 | 11/2013 | | |
| WO | WO 2014185397 A1 | 11/2014 | | |
| WO | WO-2017114948 A1 * | 7/2017 | ........... | A47C 17/162 |

OTHER PUBLICATIONS

Translation of Chinese Search Report dated Mar. 26, 2620 with respect to counterpart Chinese patent application 201580079659.8.

(56) References Cited

OTHER PUBLICATIONS

International Search Report issued by the European Patent Office in International Application PCT/EP2016/082919 dated Mar. 23, 2017.

\* cited by examiner

SLEEPING OR RECLINING FURNITURE, ANALYZING UNIT FOR A SENSOR OF SLEEPING OR RECLINING FURNITURE, AND METHOD FOR ANALYZING SIGNALS OF A SENSOR

CROSS-REFERENCES TO RELATED APPLICATIONS

This application is the U.S. National Stage of International Application No. PCT/EP2016/082919, filed Dec. 30, 2016, which designated the United States and has been published as International Publication No. WO 2017/114948 and which claims the priorities of German Patent Applications, Serial No. 10 2015 107 148.5, filed Dec. 30, 2015, 10 2016 109 524.9, filed May 24, 2016, and 20 2016 105 633.0, filed Oct. 7, 2016, pursuant to 35 U.S.C. 119(a)-(d).

BACKGROUND OF THE INVENTION

The invention relates to an analyzing unit for connecting to at least one sensor which can be coupled to sleeping or reclining furniture in order to detect vibrations, movement, and/or sound. The invention furthermore relates to sleeping or reclining furniture, in particular a bed, comprising such a sensor and an analyzing unit connected thereto, and also a method for analyzing signals of such a sensor.

In the clinical field, monitoring devices are known, which monitor the respiration and/or cardiac activity of a patient in sleep, to be able to engage in the event of worrying cardiac function and circulatory parameters.

In the meantime, devices for monitoring the sleep state on the basis of physiological parameters have also become commercially available for nonclinical purposes. These devices, which are placed on a night table, for example, detect noises and/or movement states during sleep by means of microphones and/or cameras. A sleep state is derived from the detected items of information and the time curve thereof is recorded. The recorded sleep curve can subsequently be retrieved and analyzed. It can be informative about how deep and restful the sleep has been.

In addition to systems which use camera and/or microphone, a sensor-based system is known, in which a pressure-sensitive sensor strip is laid over the mattress and in which the sensor strip is connected to a mobile telephone (smart phone), which records the sensor data. A heart rate and a respiratory rate, inter alia, are derived from the sensor data.

The mentioned nonclinical systems have the disadvantage of restricted ability to analyze the recorded items of information, since the sensor data are present in isolated form in the mobile telephone.

Document US 2015/0199484 A1 describes a system for automated medication dosing and delivery in a nonclinical environment. In the ascertainment of the medication dosing, measured patient data are also taken into consideration, inter alia, a sleep behavior. Measured data are transmitted for analysis to a computer, which does not necessarily have to be set up on location in the nonclinical environment.

In the case of a comprehensive monitoring of the sleep state on the basis of sensors which measure vibrations, movement, and/or sound, extensive quantities of data arise, the transmission of which to an external computer for analysis can exceed an available transmission bandwidth.

It is an object of the present invention to provide an analyzing unit for a sensor of sleeping or reclining furniture and sleeping or reclining furniture equipped therewith, which enable comprehensive monitoring of the sleep state while incorporating external points, without being subject to a high data transmission bandwidth. It is a further object to specify a suitable method for analyzing signals of the sensor.

SUMMARY OF THE INVENTION

This object is achieved by an analyzing unit or sleeping or reclining furniture comprising such an analyzing unit, respectively, and also a method having the respective features of the independent claims. Advantageous embodiments and refinements are specified in the dependent claims.

An analyzing unit according to the invention is designed to process and analyze the signals of the at least one sensor and to detect physiological parameters of at least one person using the sleeping or reclining furniture and to transmit data which contain the detected physiological parameters to at least one external component.

A method according to the invention for analyzing signals of at least one sensor, which is coupled to sleeping or reclining furniture for detecting vibrations, movement, and/or sound, has the following steps: Sensor data which the sensor provides are detected at a first repetition frequency. The sensor data are then analyzed in the local analyzing unit and values of at least one physical parameter are ascertained at a second repetition frequency which is lower than the first repetition frequency. The ascertained values of the physiological parameter are transmitted to an external component which is more remote from the sensor than the analyzing unit.

According to the invention, sensor data are thus detected from the sensor signals at a defined first repetition rate, also called sampling rate, these data are then locally analyzed to determine one or more physiological parameters. This is performed at a second, lower repetition frequency. The ascertained values are then transmitted to the external component and not the sensor data themselves. A significant data reduction for the data to be transmitted is achieved by the local analysis. To be able to analyze the sensor signals in an informative manner with respect to vibrations, data rates for the sensor data having sampling rates in the range of kilohertz are reasonable. The physiological parameters ascertained therefrom, in contrast, are also informative if only one value per second or even per minute is provided. The data volume to be transmitted can thus be strongly reduced by the local analysis.

Due to the data transmission to and/or a data exchange with the external component, the detected and pre-analyzed items of information can be put into context with other items of information, whereby synergy effects may be used, on the one hand. On the other hand, transmitting detected and pre-analyzed data to the external component facilitates long-term storage, archiving, and more computing-intensive analysis than is possible locally in the analyzing unit.

In one advantageous embodiment, the analyzing unit is designed for transmitting the data to or for exchanging data with an external mass storage device as the external component. In particular, the external mass storage device can be a cloud. A high level of availability and also long storage duration of the data can thus be ensured. The data can easily be provided to various further instances for analysis or comparison. Such a cloud can be a storage space offered by an external provider, which is provided in a decentralized and/or distributed manner by servers, which are reachable via the Internet. On the other hand, it can also be a so-called personal cloud, in which a storage location is provided locally, for example, in the form of an NAS (network attached storage) storage unit, which is reachable in an intranet. Finally, a mass storage unit connected directly in a wired manner to the analyzing unit would be understood in this meaning as a cloud. Other forms of a wired, or more precisely a circuitry-connected cloud comprise USB mass storage sticks or memory cards such as SD cards.

In a further advantageous embodiment, the analyzing unit is designed for transmitting the data to or for exchanging data with a component of a building automation system. The data connection between the analyzing unit and the building technology enables items of information relevant to one or the other side to be able to be exchanged, and thus an added value to be provided for the user of the system. For example, items of information of the analyzing unit which relate to a present sleep state can be relayed to the building technology, for example, to open or close roller blinds and/or windows automatically via the building technology, to turn on or off a room light, or to activate or deactivate an alarm system installed in the building both globally and also alternately selectively for only specific rooms, for example, all rooms with the exception of the bedroom. Vice versa, for example, the analyzing unit can also receive access to, for example, a (telephone) communication system or an alarm system via the building technology, to be able to send alarm messages if physiological parameters in a worrying range are recognized. Building technology, also referred to as building automation, is to be understood as devices for detecting environmental states and building parameters (for example, temperature, lighting, opening state of windows or doors), and also control units for controlling building components (for example, lamps, heating systems, ventilation systems, window or door opening or closing devices, roller blind controllers) which act on building parameters. The building technology can be at least partially permanently installed or also, possibly also in parts, temporarily associated with the building.

In a further advantageous embodiment, the analyzing unit is designed for transmitting the data to or for exchanging data with a control unit of an electric motor furniture drive. In this manner, components of the control unit which are already provided in the electric motor furniture drive can also be used for the analyzing unit, for example, a power supply unit, communication devices, and/or a housing including the connection options. Moreover, a wiring of the sensor is simplified if the existing structure of the electric motor furniture drive is used. Furthermore, the analyzing unit can then preferably be integrated into the control unit of the electric motor furniture drive. Moreover, information transmitted to the control unit of the electric motor furniture drive can be used directly thereby to control suitable actions of the furniture drive. For example, it can be provided that upon recognition of specific sleep states, for example, shortness of breath or snoring, an adjusting motor of the electric motor furniture drive is activated, for example, to change the position of a back or foot part of the bed, whereby in general the person also changes his or her sleep position in the bed. Furthermore, it can be provided, for example, that a lighting device coupled to the control unit, for example, a so-called underbed lighting, is temporarily turned on if it is indicated on the basis of the data transmitted to the control unit that the person is leaving or has just left the bed.

In a further advantageous embodiment, the analyzing unit is designed for transmitting the data to or for exchanging data with a mobile device, for example, a mobile telephone, in particular a smart phone, or a tablet computer. In this case, the analysis, display, and also communication options of the mobile device can advantageously be used by the analyzing unit.

In a further advantageous embodiment, the physiological parameters detected by the analyzing unit are, for example, a heart rate (pulse rate), a respiratory frequency, a movement behavior, and/or a snoring behavior of the person. To also be able to reliably analyze small signals, the analyzing unit advantageously has a filter, in particular a low-pass or bandpass filter for signal processing. Alternatively or additionally, a first signal processing can also already take place directly at the sensor, for example, by arranging a signal amplifier and/or an analog and/or digitally operating signal filter adjacent to the sensor or integrating them into a sensor housing. A transmission of the measuring signal which is less susceptible to interference to the analyzing unit is thus achieved.

Furthermore, the analyzing unit can have a storage unit for storing a time curve of the physiological parameters. The analyzing unit can moreover have a monitoring device for comparing the physiological parameters to predefined limiting values, so that, in a case in which a health risk for the person is recognized, this person or a further person can be warned.

Furthermore, the analyzing unit is designed to extract sleep states and time proportions of the sleep states in a sleep period from the time curves. The time curves of the physiological parameters and/or the sleep states and/or time proportions of the sleep states in a sleep period are then preferably part of the transmitted data.

The analyzing unit preferably has a transmitting unit for transmitting the physiological parameters to the external component. The transmitting unit is preferably designed for wirelessly transmitting the physiological parameters to the mobile device, in particular via a WLAN or Bluetooth transmission link. If the physiological parameters are transmitted to the mobile device, a comparison of the physiological parameters to predefined limiting values can also be performed in the mobile device.

A sleeping or reclining furniture according to the invention, in particular a bed, has at least one sensor for detecting vibrations, movements, and/or sound and such an analyzing unit connected to the sensor, which is designed for carrying out the mentioned method. The advantages mentioned in conjunction with the analyzing unit and/or the method result.

BRIEF DESCRIPTION OF THE DRAWING

The invention will be explained in greater detail hereafter on the basis of exemplary embodiments with the aid of figures. In the figures.

DETAILED DESCRIPTION OF PREFERRED EMBODIMENTS

Figure 1:
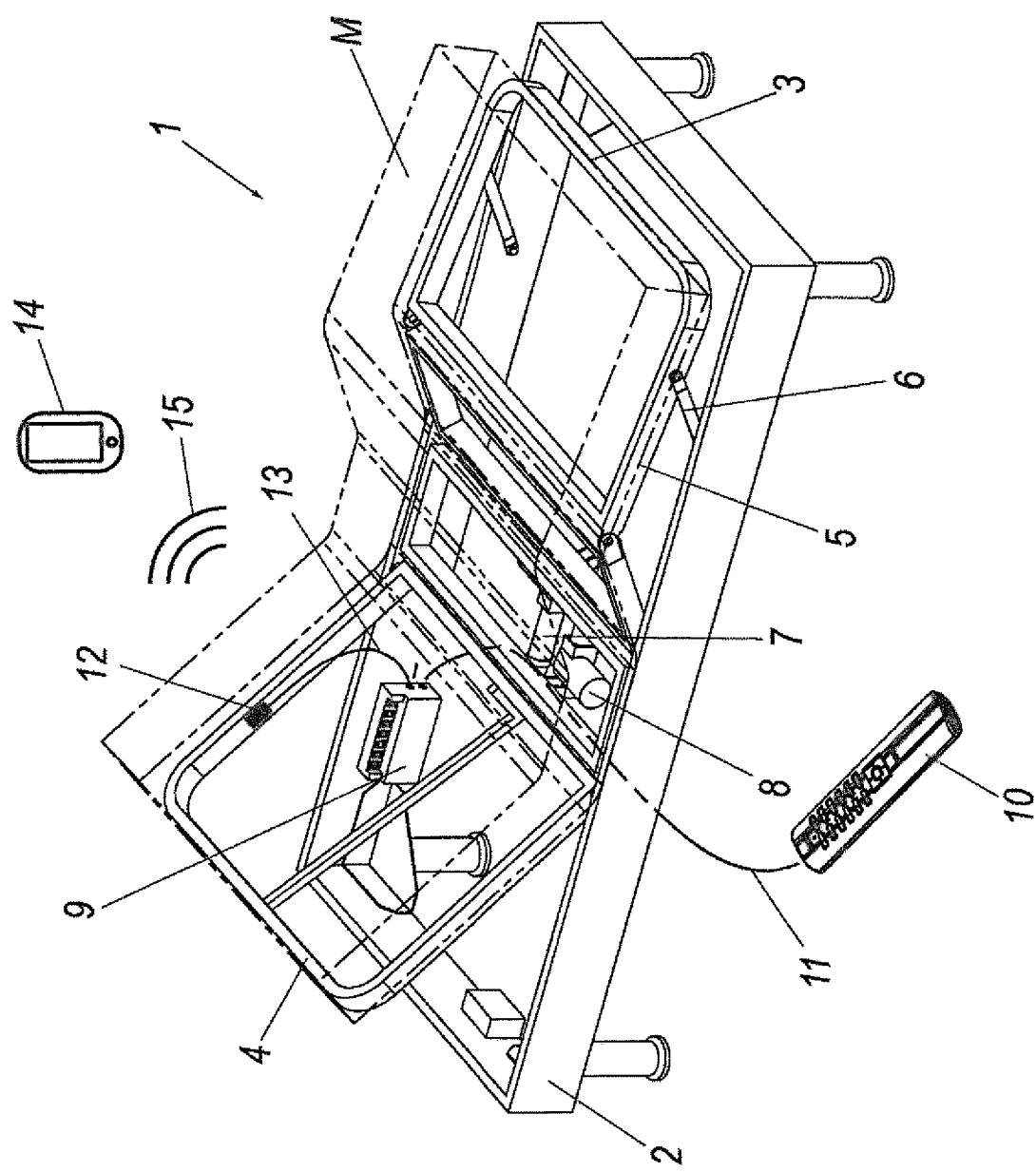
FIG. 1 shows a first exemplary embodiment of sleeping furniture comprising an electric motor furniture drive in an isometric view.

FIG. 1 shows a bed 1 as an example of sleeping furniture comprising an electric motor furniture drive. The bed 1 has at least one support element 3 for accommodating, for example, padding or a mattress M. The bed 1 can be designed as a single bed for one person or also as a double bed for multiple persons. The support element 3 is designed, for example, as a slatted frame, as a planar support surface, or the like and is on a base element 2, a framework having feet here, using which the bed 1 is set up at a setup location, for example, a floor.

The support element 3 has, in the illustrated example, a back part 4 and a leg part 5, which are arranged so they are movably mounted relative to a fixed middle part (also called middle part or seat part) or relative to the base element 2. This movable arrangement is implemented here by means of a so-called movement fitting 6. The movement is designed as displaceable and/or pivotable.

The movably mounted back part 4 and the leg part 5 are each coupled to an electric motor adjusting drive 7, 8. The back part 4 is thus coupled to the electric motor adjusting drive 7. The electric motor adjusting drive 8 is provided for the movement and/or adjustment of the leg part 5.

The electric motor adjusting drives 7, 8 are designed in the present case as linear drives. The linear drives have one or a number of electric motors, wherein a speed-reducing gear having at least one gear step is connected downstream of each motor. A further gear, for example, in the form of a threaded spindle gear, which generates a linear movement of an output element from the rotational movement of the motor, can be connected downstream of the speed-reducing gear. The last gear element or a further element connected thereto forms the output element. The output element of the respective electric motor furniture drive is connected to the respective furniture component (back part 4, leg part 5) or alternatively to a component connected to the base element 2, so that in the event of an operation of the electric motor of the respective adjusting drive 7, 8, the movable furniture components 4, 5 are adjusted relative to one another and/or relative to the base element 2.

The electric motor adjusting drives 7, 8 are connected to a control unit 9. This connection can be embodied, for example, as a pluggable cable connection, which is not shown in greater detail here. The control unit 9 has an electrical supply unit, which provides the electrical energy, for example, from a power supply network, for the electric motor adjusting drives 7, 8. For this purpose, the control unit 9 is connectable via a network cable (not shown in this example) having a network plug to a network terminal. The network plug conducts the input side network voltage via the network cable to the electrical supply unit of the control unit 9, which emits a low voltage in the form of a DC voltage on the secondary side.

Alternatively thereto, an external network-dependent power supply having network input and having secondary side low-voltage output is connected upstream of the control unit 9, which supplies the low voltage in the form of a DC voltage via the line.

In an alternative embodiment, the control unit is not arranged in a separate housing, but rather integrated into one of the adjusting drives 7, 8. This adjusting drive then represents a main drive, to which further adjusting drives can optionally be connected.

In a further alternative embodiment of an electric motor furniture drive, the control unit can be arranged distributed in the system such that each of the adjusting drives 7, 8 has a motor controller itself and has a bus communication interface, via which the adjusting drives 7, 8 are connected to one another and to further components. It can be provided in this case that at least one of the adjusting drives 7, 8 has a separate power supply unit for its power supply or for the supply of multiple or all provided adjusting drives and/or possibly further system components.

A manual operation unit 10 is provided, which has operating elements, using which the electromechanical adjusting drives 7, 8 are controllable via the control unit 9. The manual operation unit 10 can be connected via a cable to the control unit 9 in one exemplary embodiment. Alternatively, the manual control unit 10 can be provided with a transmitting device for a wireless transmission of signals to the control unit 9. The wireless transmission can be implemented by a radio transmission link, an optical transmission link (for example, for infrared light), and/or an ultrasound transmission link, wherein the control unit 9 is equipped with a respective corresponding receiving unit. Furthermore, the manual operation unit can alternatively also form the control unit for the adjusting drives, for example, by the operating current of the adjusting drives being switched directly via switches of the manual operation unit.

The operating elements can be designed, for example, as buttons and/or switches. Furthermore, the manual operation unit 10 can be equipped with a reporting element, for example, a light-emitting diode or a display unit. The reporting element is used, for example, for function display and/or feedback, error displays, etc. Furthermore, a mobile device 14 can be used for the operation of the electric motor adjusting drives 7, 8. The mobile device 14 can be designed as a smart phone. The mentioned operating elements can be formed as regions of a touchscreen.

According to the application, a sensor 12, which detects vibrations and/or sound, is provided in the illustrated bed 1. The sensor 12 is fastened in the illustrated exemplary embodiment on a frame component of the back part 4. The fastening can be a screw or rivet connection or an adhesive bond or can also be a catch or clamp connection, for example, with the aid of a spring clamp which encloses the corresponding frame component. The sensor 12 is designed, for example, as a piezoelectric component or as an electromagnetic component or as an electromechanical component and is sensitive to vibrations of the underlying surface on which it is fastened, in the present case thus for oscillations (vibrations) or movement which the frame of the back part 4 experiences. A further suitable sensor is an electromechanical sensor, for example, a micromechanical acceleration sensor.

The mentioned vibrations also comprise structure-borne sound, which is relayed by the back part. "Movements" are to be understood in particular as low-frequency vibrations and deflections of the sensor 12, the frequency of which is in the hertz or subhertz range. In addition, the sensor 12 can be sensitive to (airborne) sound waves and can function in this meaning as a microphone.

The sensor 12 is connected via a sensor cable 13 to the control unit 9. If necessary, a power supply for the sensor 12 is provided via the sensor cable 13 and signals output by the sensor 12 are relayed to the control unit 9. In an alternative embodiment, the sensor 12 can be coupled via a wireless connection, for example, a radio connection, to the control unit 9. In this case, the sensor 12 is provided with a separate power supply, for example, in the form of a possibly rechargeable battery.

In the bed 1 shown in FIG. 1, a single sensor 12 is provided by way of example. Furthermore, multiple sound and/or vibration pickups can also be combined in one sensor or in various sensors, wherein, for example, a piezoelectrically and an electromagnetically operating sound and/or vibration pickup are arranged at the same position or at various positions. The various sensor types are distinguished by characteristic frequency ranges, for which they are particularly suitable. The combination of various sensor types enables a particularly broad frequency spectrum to be able to be recorded and analyzed.

The control unit 9 comprises an analyzing unit for processing and analyzing the signals supplied by the sensor 12. The analyzing unit comprises, for example, amplifiers and filter units, which enable certain physical functions of a person located in the bed 1 to be inferred from the signal transmitted by the sensor 12. In particular, the analyzing unit is configured for the purpose of ascertaining physiological parameters of the person from the signals of the sensor 12. Such parameters relate, for example, to cardiac and circulatory functions and comprise, for example, a heart rate and a respiratory rate. Furthermore, it can be ascertained whether the person located in the bed is snoring. Moreover, movements of the person are detected. Details on the ascertainment of the mentioned parameters from the signals of the sensor 12 will be explained in greater detail hereafter in conjunction with FIGS. 3 and 4.

The determined parameters are transmitted either immediately or after buffering in the control unit 9 in a direct data transmission 15 as wireless signals to a mobile device 14 as an external component. The mobile device 14 can be in particular a commercially available mobile telephone ("smart phone") or a tablet computer and is equipped with corresponding software ("app"), which enables analysis and preferably graphic display of the time dependence of the ascertained sleep parameters. WLAN (wireless local area network) or Bluetooth, for example, can be used as the transmission link for the direct data transmission.

Alternatively to the direct data transmission 15, according to all embodiments, indirect data transmission can exclusively or additionally be provided if the data stream is conducted via other components and possibly buffered therein. Buffering can take place temporarily and after completed data transmission a temporary buffer can be erased again, so that it is available again for subsequent further buffering. In one embodiment, the cloud is considered as a buffer. An indirect data transmission is provided, for example, if the mobile device 14 is used like a type of modem, which receives the data of the analyzing unit by means of a first transmission fink, for example, in the form of a Bluetooth transmission link, and transmits them by means of a further transmission link, for example, WLAN or mobile wireless, to an external component, for example, in the form of the cloud.

Moreover, a comparison of the measured physiological parameters to predefined limiting values for these parameters can be provided in the analyzing unit of the control unit 9. If the ascertained parameters are transmitted immediately, i.e., without long buffering in the control unit 9, during the sleeping phase to the mobile device 14, such a comparison can alternatively or additionally take place therein. If the parameters exceed or fall below the limiting values or one or more of the parameters leave a predefined range, it is provided that the analyzing unit or the mobile device 14 outputs an alarm signal. This alarm signal can be output optically and/or acoustically directly by the analyzing unit and thus, for example, the control unit 9 and/or the mobile device 14. Alternatively or additionally, it can be provided that the mobile device 14 emits an alarm message via a further wireless transmission link (not shown here) (for example, WLAN, mobile radio network). In this manner, a further person can be informed if undesired sleep parameters are shown. The illustrated bed 1 and/or the electric motor furniture drive comprising the sensor 12 can thus also be used for clinical monitoring and/or for patient monitoring or for monitoring small children to protect from sudden infant death. For example, an alarm message can be emitted if a person has left the bed, possibly if a person has left the bed since a predetermined time, or if no physiological parameters or only physiological parameters considered to be critical are detected.

Further unusual sleep parameters can be in the form of apnea, snoring, or even absences of the previously sleeping person. In the case of the last mentioned, a presence or an absence check of the person takes place.

In the illustrated exemplary embodiment, the sensor 12 is arranged on a frame element of the back part 4. This can take place directly or via a carrier element. The latter offers a simpler retrofitting option of the sensor on an already provided bed 1. Other arrangements on the sleeping furniture, i.e., the illustrated bed 1, or elements connected thereto, such as the mattress M laid thereon, are possible. The sensor 12 can be installed, for example, on a slatted frame (not visible here). Installation secure against slipping in or on the mattress M is also possible. Furthermore, the use of multiple sensors 12, possibly of different types, which are positioned at identical or different points in or on the bed 1 is possible.

The arrangement of each sensor ideally takes place in regions of the bed 1 which lie adjacent to the sound-generating body parts of the monitored person(s), i.e., for example, in the heart/lung region and in the region of the throat and/or the mouth opening. Conceivable attachment locations are the back part 4. Other attachment locations are the seat or middle part, which extends between back part 4 and leg part 5.

The connection of the sensor 12 to the analyzing unit of the control unit 9, which is arranged inside the bed 1, prevents the sensor cable 13 having to be laid outside the bed 1. The fixing of the sensor 12 in or on the bed 1 ensures correct positioning of the sensor 12 at all times and thus reliable analysis of the data of the sensor 12.

Figure 2:
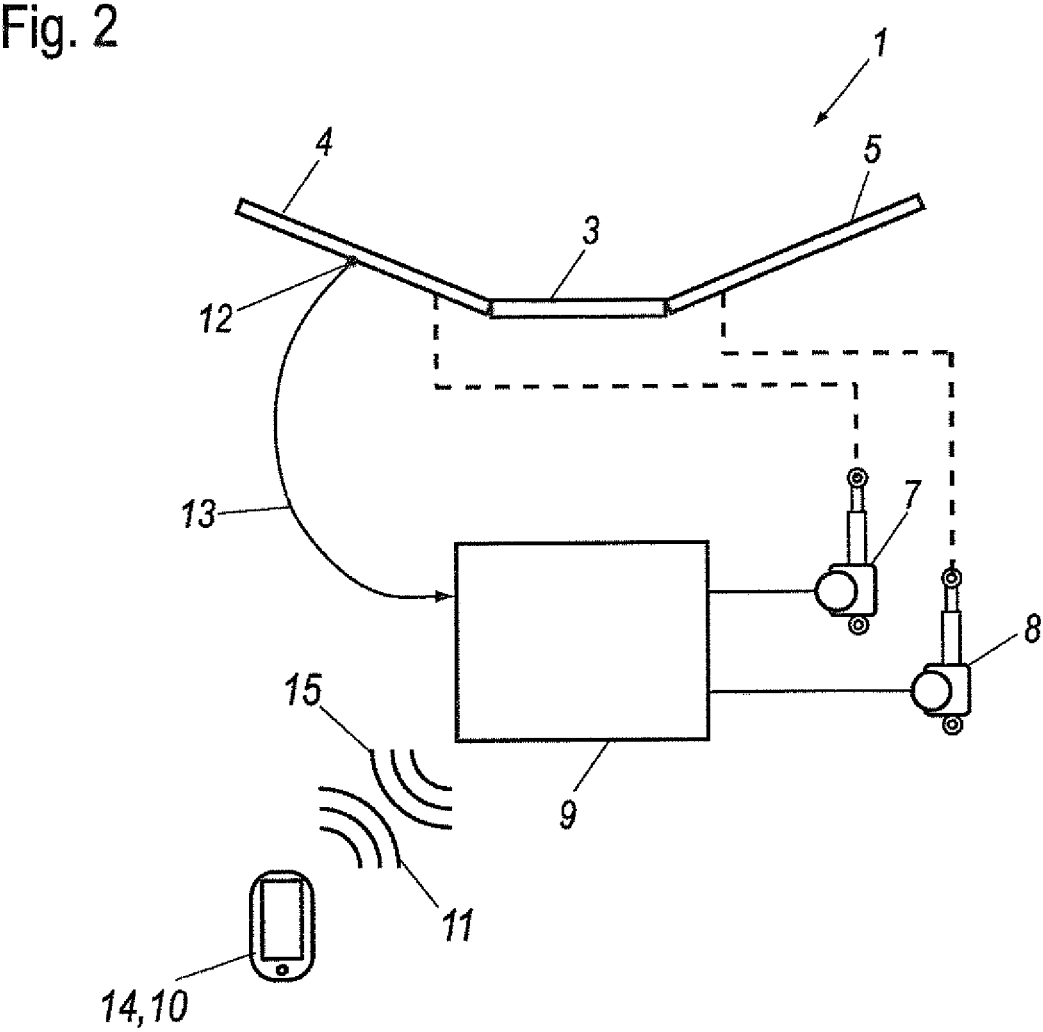
FIG. 2 shows a second exemplary embodiment of sleeping furniture comprising an electric motor furniture drive in a schematic block diagram.

FIG. 2 shows a second exemplary embodiment of sleeping furniture comprising an electromechanical furniture drive and an integrated sensor 12 in a schematic block diagram. A bed 1 is again shown as an example of sleeping furniture. Identical reference signs identify identical or identically acting elements as in FIG. 1 in the exemplary embodiment of FIG. 2.

The electric motor furniture drive according to FIG. 2 corresponds to that shown in FIG. 1 in its basic construction. Reference is hereby made to the preceding description.

In contrast to the exemplary embodiment of FIG. 1, in the present case the mobile device 14 also assumes the function of the manual operation unit 10. Corresponding software ("app") for the function as the manual operation unit 10 is again installed on the mobile device.

The transmission link between the mobile device 14 and the analyzing unit of the control unit 9 is embodied as bidirectional, so that control instructions to the adjusting drives 7, 8 can be transmitted from the mobile device 14 used as the manual operation unit to the control unit 9, and data which relate to the sleep state can be transmitted from the control unit 9 to the mobile device 14.

In the exemplary embodiments of FIGS. 1 and 2, the analyzing unit for the signals of the sensor 12 is integrated into the control unit 9. Alternatively, it is possible to form the analyzing unit separately from the control unit 9 in a separate housing. The analyzing unit can then be electrically coupled to the control unit 9, for example, via a data line, to transmit the ascertained physiological parameters. Components of the control unit, for example, a communication interface for wireless data transmission, can then advantageously also be used and do not need to also additionally be provided in the analyzing unit. A use of an autonomous analyzing unit detached from the control unit 9 is also possible, in particular if a transmission unit is already provided in the housing of the analyzing unit for the wireless transmission of the ascertained physiological parameters and/or preprocessed signals of the sensor 12 to an external component, for example, the mentioned cloud or the mobile telephone. The transmission can be designed as bidirectional in this case.

A further advantage of a separate analyzing unit is the provision of a uniform system for various bed types having various control units 9. Therefore, a first analyzing unit for single beds having a variety of variants and adjusting drives 7, 8 can be used, and also a further analyzing unit can be used for use in double beds.

Figure 3:
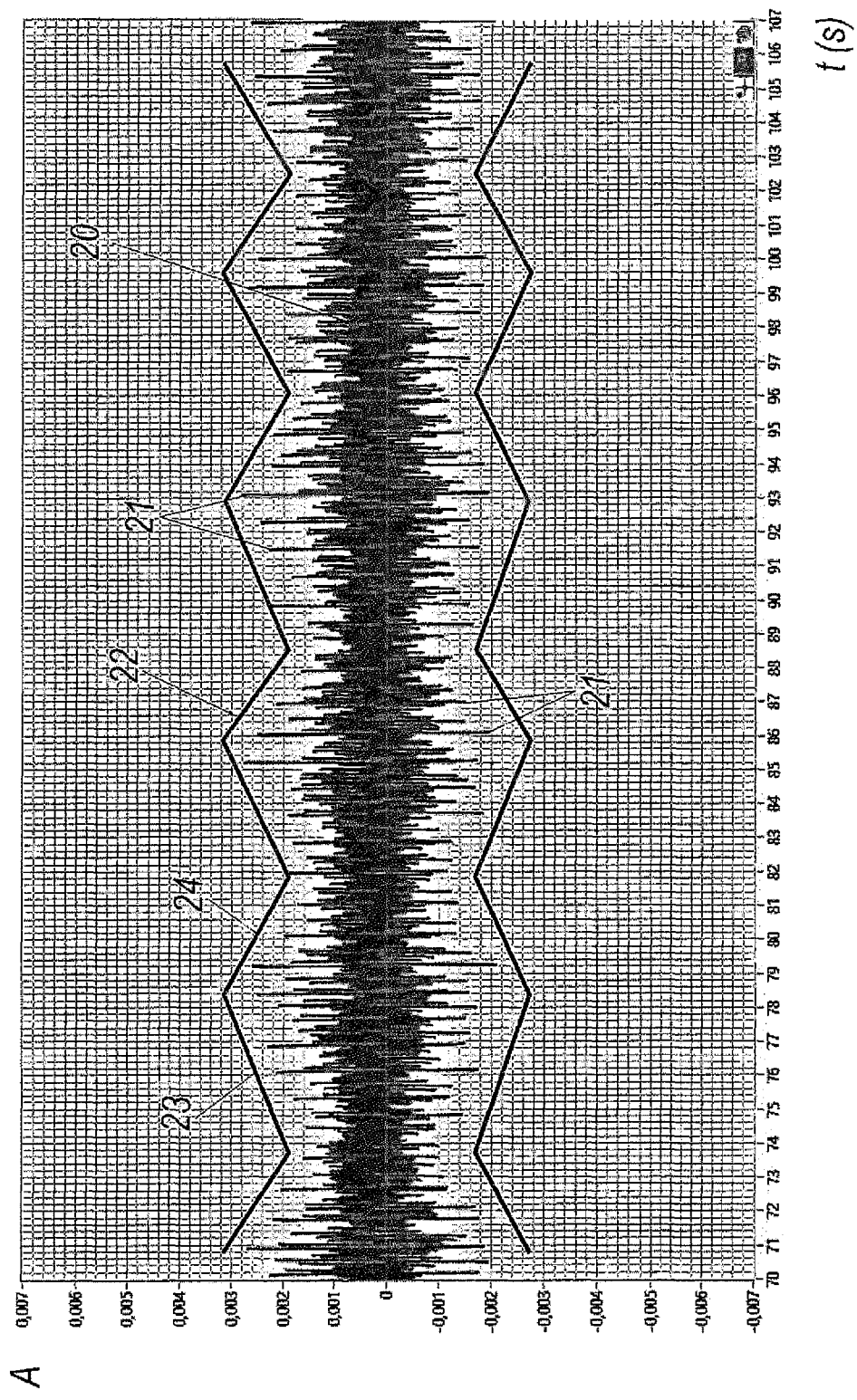
FIG. 3 shows a reproduction of a time dependence of sensor data.

FIG. 3 shows a detail of a measured signal 20 of the sensor 12 in a diagram. The time curve t in seconds is indicated on the horizontal axis. A signal amplitude A in arbitrary units is shown on the vertical axis. The signals of the sensor 20 are recorded and/or digitized in this case at a first repetition frequency (sampling rate) in the range of kilohertz (kHz).

The portion shown of the signal curve of the signal 20 is during a calm sleep phase without movement and without snoring of the observed person. A movement of the person is expressed in amplitudes which exceed those shown by a factor of several tens to hundreds. Movements may therefore be identified very easily. A snore and the vibrations accompanying it can also be clearly differentiated from the illustrated signal curve, since they are reflected in an amplitude greater by multiple times.

In the curve of the signal 20 shown in FIG. 3, regular peaks 21 are observable, which originate from the heartbeat of the person and are referred to as heartbeat peaks 21 hereafter. A heart rate can be ascertained from the interval of the heartbeat peaks 21. The time interval of adjacent heartbeat peaks 21 permits statements about the pulse uniformity, which can be a measure of the depth of the sleep.

Furthermore, it can be seen in FIG. 3 that the amplitude of the heartbeat peaks 21 varies regularly at a lower frequency. This variation is illustrated by an envelope curve 22. The envelope curve 22 displays alternating rising flanks 23 and falling flanks 24. The curve of the envelope curve 22 is correlated with the breathing of the person. The rising flanks 23 identify an inhalation phase and the falling flank 24 identifies an exhalation phase.

The example of FIG. 3 shows how cardiovascular parameters can be concluded from the signals of the sensor 12, in the present case pulse and respiration. In a similar manner, further sleep parameters, such as movement states and snoring, can be ascertained.

Filtering of the raw signals of the sensor 12 is carried out, in particular by means of a low-pass filter, for the analysis of the signals 20. The use of a bandpass filter having suitable base frequencies is also possible. Low-pass or bandpass filters are used to eliminate interfering frequencies. A signal-strength-dependent amplification (automatic gain control) can also take place in this case. The processing of the signals is preferably carried out with the aid of a digital signal processor (DSP). In particular, it can be provided that the signals 20 are subjected to a spectral analysis, for example, by a fast Fourier transform (FFT), to be able to analyze the frequency components contained in the curve of the signals 20. Filtering of the obtained spectra can also be performed, for example, by only further processing frequency components having a specific minimum amplitude and discarding others.

The sensor 12 can additionally or alternatively also be used for monitoring the correct function of the electric motor drive. An actuation of the adjusting drives 7, 8 results in a movement of the moving furniture parts, for example, of the back part 4 and/or the leg part 5. In addition, the actuation of the adjusting drives 7, 8 results in vibrations of these furniture parts and also of the entire furniture, which are also detected by the sensor 12. These vibrations occur in a typical frequency range. The signal curve reflects the motor movement of the adjusting drives 7, 8. A first typical relevant frequency range is in the range of the motor speed of the motors of the adjusting drives 7, 8. Faults on the motor itself or an output gear wheel are shown in this frequency range. A further typical relevant frequency range corresponds to an integer fraction according to a transmission ratio of the gear, which is approximately 1:30 to 1:50. Faults in downstream gear stages or roller bearings are indicated in this frequency range. A third typical frequency range is in the range of squeaking noises of hinges, which are part of a furniture fitting. Shape and amplitude are, on the one hand, typical for the adjusting drive 7, 8 used, on the other hand, they give information about the correct function of the adjusting drives 7, 8 and the wear state thereof.

An overload of one of the adjusting drives 7, 8 can also be recognized on the basis of the signal form of the signals of the sensor 12. The sensor 12 can thus function, for example, as a pinch protection, wherein the control unit 9, in the event of overload of one of the adjusting drives 7, 8, stops this drive and/or causes it to run in the opposite direction. An underload on the adjusting drive 7, 8 can also be an indication of pinching, for example, if a furniture part (back part 4, leg part 5) is released and the adjusting drive 7, 8 is operated nearly without force, this indicates pinching of a body part under the moving furniture part which is sinking down. An adjusting drive 7, 8 operated without load is also identifiable on the basis of the signals of the sensor 12. An overload can be characterized and sensorially detectable and analyzable if particularly low frequencies in a range typical for motor running frequencies and gear running frequencies are provided with corresponding amplitude at the same time.

Figure 4:
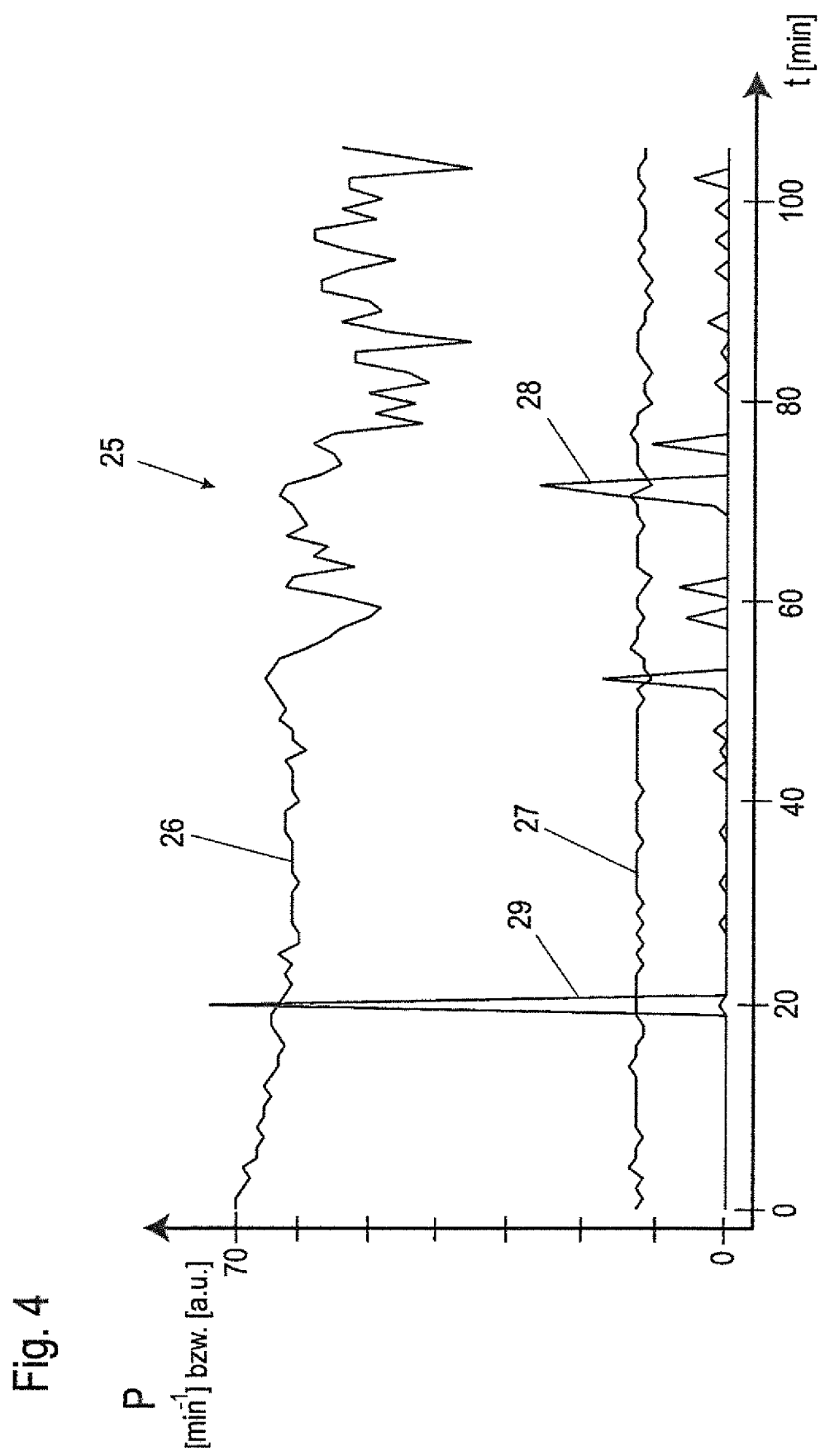
FIG. 4 shows a reproduction of a time dependence of physiological parameters.

FIG. 4 shows exemplary physiological parameters P which were extracted from measured signals 20 of the sensor 12, as illustrated by way of example in FIG. 3. According to the application, a local analysis takes place in this case to ascertain the various physiological parameters. For example, each extracted parameter P can be ascertained once per minute. In this manner, the large data volume of the digitized signals 20 of the sensor 12 is advantageously reduced to a significantly smaller quantity of data. The analysis therefore already takes place in the control unit 9 and/or in the analyzing unit, which is contained therein or also embodied separately.

In the illustrated example, the physiological parameters P relate to a pulse rate (heart rate), a respiratory rate, a movement behavior, and a snoring behavior. However, it is also conceivable to only extract a subgroup of these exemplary physiological parameters P or also further physiological parameters from the measured sensor data 20. Reference is made to the following statements with respect to details of the extraction of the physiological parameters P.

As illustrated in FIG. 4, the physiological parameters P are extracted as data 25 at a second repetition frequency (data rate) in the form of time series and stored and further analyzed in the further proceedings. In FIG. 4, the data 25 are plotted over a horizontal time axis, which shows a time t in minutes. The physiological parameters P are indicated in different units on the vertical axis.

The pulse rate is shown in a first time series 26 in the unit 1/min (minutes). To form the first time series 26, for example, the number of the heartbeats is determined from the sensor data 20 and counted over a minute. The corresponding value forms a data point in the time series 26. However, it is also conceivable to ascertain it over a shorter or longer period of time and, for example, to provide two measurement points per minute or also only one measurement point every 2 or 5 minutes. A greater time interval of the data points in the first time series 26 reduces the amount of data of a time series, but results in averaging, which no longer permits short-term physiological irregularities to be recognizable. A minute-by-minute detection represents a good compromise of quantity of data and informative power of the data in this respect. The scope of data of the first time series 26 is approximately 4 kB for a time length of 8 hours, if one data point per minute is stored in the time series 26. In any case, the data rate in the first time series 26 and the further time series described hereafter is significantly lower in this case than the data rate using which the signals 20 of the sensor 12 are sampled and further processed.

A second time series 27 represents the respiratory rate, also in the unit 1/min. One data point is preferably also saved here for each minute.

A third time series 28 shows a movement in sleep extracted from the raw data 20. This is indicated in arbitrary units. According to the depiction in FIG. 4, numerous small signals are visible close to the zero line of the third time series 28, while three small signals and two medium-size signal amplitudes 28 are provided as a measure of the movement behavior of the sleeping person.

A fourth time series 29 finally represents a snoring behavior extracted from the sensor data 20, also stored in a minute cycle. In the exemplary detail of approximately 100 minutes, which is shown in FIG. 4, a snore has only been detected once at approximately t=20 minutes.

Various scenarios for transmitting data to and for exchanging data with external components are described hereafter in conjunction with FIGS. 5 to 8.

Figure 5:
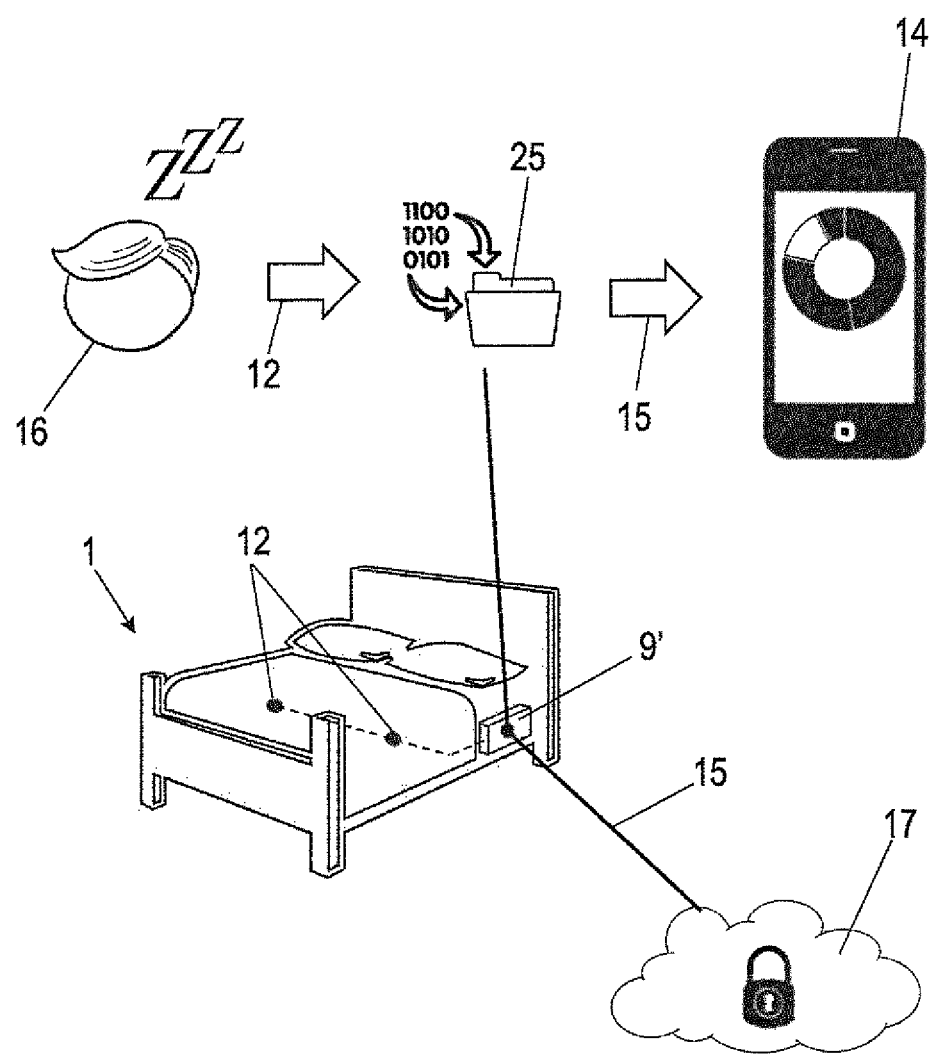
FIGS. 5-8 show various scenarios for the transmission and analysis of data to and for the exchange of data with various external components in a schematic sketch in each case.

In a first scenario according to FIG. 5, a double bed is shown as the bed 1 by way of example, which is equipped with two sensors 12 here, which are connected to an analyzing unit. In contrast to the exemplary embodiments illustrated in FIGS. 1 and 2, in the present case an analyzing unit 9' is formed separately from a control unit (not shown in FIG. 5) of an electric motor furniture drive. It is apparent that the analyzing unit 9' of the exemplary embodiment of FIG. 5 can also be integrated into a corresponding control unit or can be connected to the control unit for data exchange. As indicated in the upper part of the figure, data of at least one person 16 are detected by the sensor or sensors 12 and these sensor data are analyzed in the analyzing unit 9' to obtain the data 25. These data 25, which comprise, for example, time series 26-29, as shown in FIG. 4, are firstly preferably stored in the analyzing unit 9'.

The further analysis of the data 25 takes place in two different ways, which can be followed alternatively or simultaneously. On the one hand, an immediate analysis with respect to values of the physiological parameters which physiologically deviate from a normal value and in particular are worrying can take place. For example, as already mentioned in conjunction with FIGS. 1 to 3, limiting values can be stored, which cause an immediate reaction if the parameters exceed or fall below them. These limiting values can be stored, for example, in the analyzing unit 9', so that a warning signal is emitted immediately by the analyzing unit 9' if values of one or more of the physiological parameters P which deviate from the normal state or are worrying are detected on the basis of the limiting values.

A second possible way of analysis relates to statements on the sleep behavior, which cannot be made on the basis of instantaneous values, but rather only on the basis of the time series (cf. time series 26-29 according to FIG. 4). This analysis only meaningfully takes place at the end of a sleeping period. The end of a sleep period is either recognized on the basis of the physiological parameters P themselves, for example, if no signals corresponding to the person are still provided over a predetermined time interval, or also on the basis of a manual input, which the person 16 performs, for example, at an operating element of the analyzing unit 9'. Alternatively thereto, further items of information which the analyzing unit receives, for example, via a coupling to a device of the building automation, can also be used to ascertain the end of a sleep period, for example, if it is communicated by the device for building automation that a coffee machine or a music system has been turned on. If the end of the sleep period is recognized by the analyzing unit 9', vice versa, the device for building automation can be informed of the end of the sleep period and in turn can turn on (kitchen) devices such as the mentioned coffee machine or the music system.

After the end of the sleep period, the data 25 are already preferably analyzed in the analyzing unit 9' for the presence of specific sleep states, also called sleep phases. Sleep phases differ, for example, due to the level and/or variation of the pulse and/or the movement within the sleep. For example, two different sleep phases for t<50 minutes and t>50 minutes are easily recognizable on the basis of FIG. 4. The first sleep phase at t<50 minutes is distinguished by a heart rate which only varies slowly, with little movement in sleep at the same time. The second sleep phase at t>50 minutes shows significant jumps and variations in the heart rate and a significant rise of the movement. Certain ones of the sleep phases are particularly significant for restful sleep. In an analysis of the data 25, the presence of the various sleep phases is recognized and the proportion thereof in the overall sleep duration is ascertained. The data 25 thus analyzed enable the sleep quality to be summarized in a variable, for example, as a numeric value of 0 to 100. The items of information about sleep phases and proportions of the sleep phases in the overall sleep duration or the sleep quality can be prefixed, for example, as a header to the data 25.

The respective sleep phases, which are also referred to in the literature as sleep stages, are understood as the classification of the sleep according to differing intensity. The sleep phases light sleep (N1), sleep (N2), and extensive deep sleep (N3) and also REM (rapid eye movement) sleep (R) are known from the literature. The sleep phases mentioned according to the application are to be limited by way of example to four sleep phases. In other embodiments of the allocation and assignment of the data 25 to the respective sleep phase, at least two sleep phases can be used. As an alternative, the number of the sleep phases can also be designed as adaptable from the scope of the available data, for example, if a limited quantity of data is available for analysis by the analyzing unit 9' due to a very short sleep duration.

The at least one sensor 12 or the at least one sensor signal thus permits inferences about the respective sleep phase. The data 25 which are derivable from the sensor 12 or the sensor signal and are provided differ from the items of information obtained from polysomnography, since the at least one sensor 12 according to the application cannot detect brain activity. However, it has been shown that by detecting the physiological parameters mentioned according to the application by way of the at least one sensor 12, signals, data 25, and items of information are provided which permit inferences about the respective sleep phase according to a downstream processing and filtering and analysis. As a computation result it is therefore also possible to output a single numeric value characteristic of the sleep performed. For this purpose, it is then expedient if an arithmetical weight is assigned to each sleep phase. Alternative computation results can summarize sleep phases in isolated form.

It has been shown that the respective curve of at least one time series changes characteristically as a function of the respective sleep phase. FIG. 4 illustrates the change of the characteristic curve of the first time series 26 along the abscissa, wherein a significant change of the signal curve is recognizable. While in the left half of the image, the signal assumes a nearly uniformly monotonously falling curve, strong variations are applied to the signal curve in the right half of the image. Various sleep phases can thus be recognized by a computer-assisted analysis of the respective signal curve of the respective time series 26, 27, 28, 29. Thus, for example, statistical analyses can be helpful, wherein the level of a statistical computation measure can be used or serve as a measure for determining a sleep phase and even a sleep quality. For example, the standard deviation as a statistical computation measure of the signal curve of the first time series 26 in the left half of the image is significantly less than the standard deviation of the signal curve of the first time series 26 of the right half of the image.

The computer-assisted analysis furthermore comprises a logical linkage of conditions and threshold values and can be applied solely to a respective time series 26, 27, 28, 29 or—as presented here by way of example on the basis of the time series 26—can take place following the above-mentioned statistical analysis. Various statements can be assigned as a result of the at least one statistical computation measure from the level thereof.

A statistical computation measure of lesser level can be assigned to a first statement. A statistical computation measure having a level within a predefined span can be assigned to a further statement. A statistical computation measure in a predefined level with simultaneously provided statement of the same of another time series can in turn be assigned to a further statement. Each statement can be depicted as a computer numeric value. Each statement or the computer consideration together of selected statements stands for the depiction of the respective provided sleep phase and/or for the depiction of the respective provided sleep quality value. The above-mentioned extraction of the physiological parameters P from the signals of the sensor 12 or from the data which are generated from the signals of the sensor 12 takes place on the basis of this method.

The known measures, for example, standard deviation, mean value, variance, interval limits, normal distribution, differentiation according to time, variation coefficient, and the like come into consideration as the statistical computation measures and/or the auxiliary measures thereof.

In the exemplary embodiment illustrated in FIG. 5, after ending sleep, the assembled sleep data, i.e., the proportions of the various sleep phases and the sleep quality value ascertained therefrom, are transmitted via a direct data transmission 15, preferably a wireless data transmission via Bluetooth or WLAN, to the mobile device 14. These items of information can therefore be displayed in appropriately processed form to the person 16 after ending sleep. In an alternative embodiment, it is conceivable to also transmit the data 25 themselves to the mobile device 14 as the external component, whereupon an analysis of the sleep phases takes place in the mobile device 14.

To also enable a longer-term analysis and checking of the sleep behavior, it can additionally be provided that the data 25 and/or the items of information ascertained therefrom about the sleep phases are transmitted via a corresponding data stream 15 to an external storage location, a so-called cloud 17 as a further external component. Since these are possibly sensitive personal data, such transmission and storage take place in a secured manner, preferably encrypted. The data can be stored for a longer period of time in the cloud 17 because of a greater storage capacity than is reasonable in the analyzing unit 9' itself.

Furthermore, different types of data 25 are provided for storage in the cloud 17. Exclusively a person 16 has writing and reading rights to personal data of the person 16, among them also the physiological data. System-specific data 25, which relate to notices about the respective status of an adjusting drive 7, 8 or the control unit 9 or the analyzing unit 9', and also data corresponding to the wear of these components or data corresponding to the wear of the bed 1 or to the wear of a mattress, can also be stored or at least buffered in the cloud 17. In case of service, the service center 18 thus has the option of viewing selected data for the purpose of remote diagnosis.

Furthermore, the option exists of feeding a selection of system-specific data 25 beforehand to a statistical analysis.

In the scope of the present application, the term "cloud" is to be understood broadly in this case. On the one hand, it can be a storage space offered by an external provider, which is provided in a decentralized and/or distributed manner by servers, which are reachable via the Internet. On the other hand, it can also be a so-called personal cloud, in which a storage location is provided locally, for example, in the form of an NAS (network attached storage) storage unit, which is reachable in an intranet. Finally, a mass storage unit connected directly in a wired manner to the analyzing unit would be understood in this meaning as a cloud. Other forms of a wired, or more precisely a circuitry-connected cloud comprise USB mass storage sticks or memory cards such as SD cards. These cloud-forming storage elements can be provided at various locations and components. Smart phone, analyzing unit 9', control unit 9, bed 1, storage module of the building technology 19, etc. are to be mentioned as exemplary locations.

Figure 6:
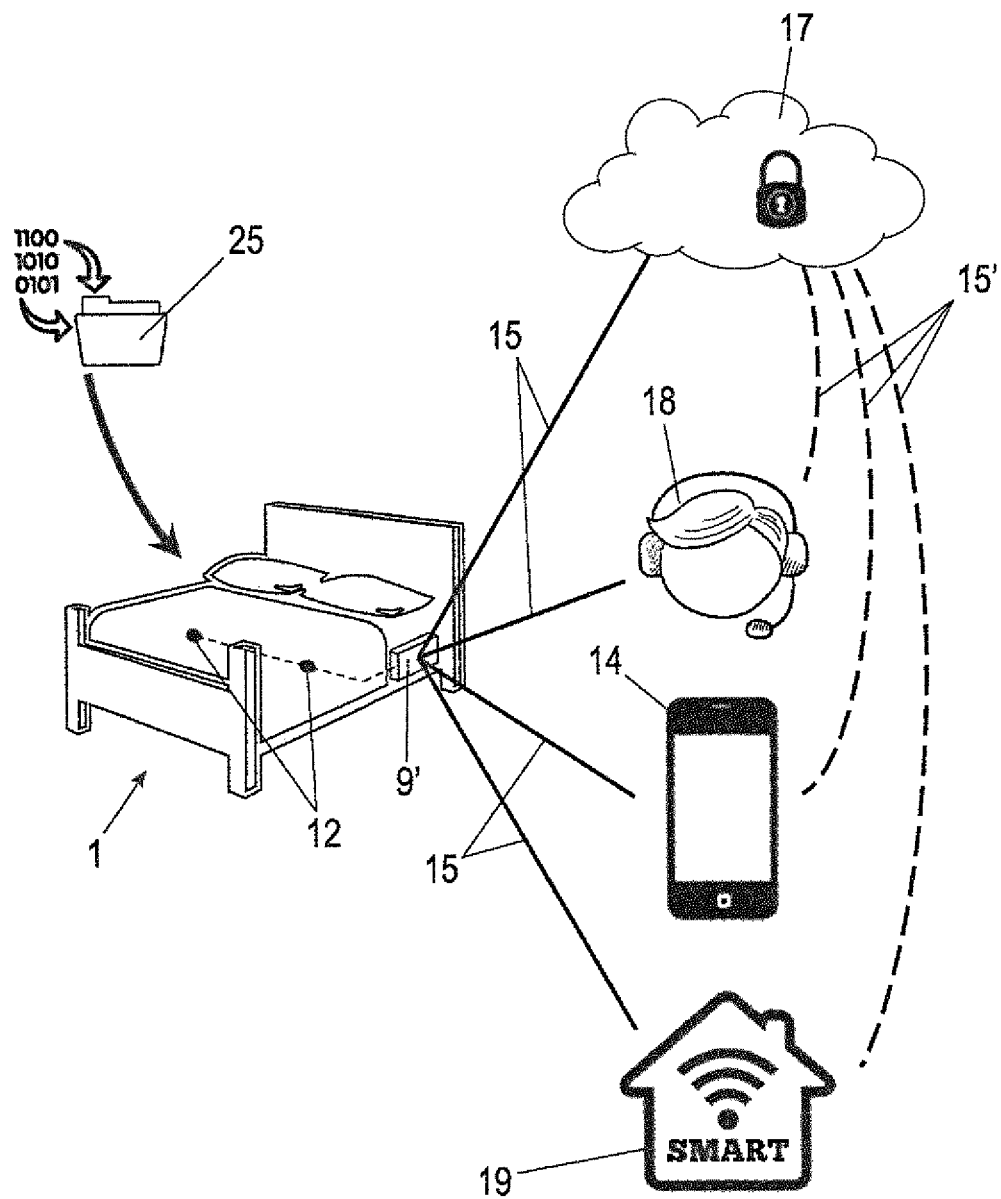

FIG. 6 shows a further exemplary embodiment of an analyzing unit 9' for sensor signals of the sensor 12 having options expanded in relation to the example of FIG. 5 for data storage, transmission, and analysis.

The system shown in FIG. 6 corresponds in principle to that shown in FIG. 5, and the description thereof is hereby referred to. In the exemplary embodiment of FIG. 5, the analyzing unit is designed for data transmission to the mobile device 14 and the cloud 17. In the exemplary embodiment of FIG. 6, the analyzing unit 9' is additionally also designed for a data exchange via a direct data link 15 with a service center 18 and devices of a local building automation technology 19, referred to as building technology 19 in short hereafter. The service center 18 and the building technology 19 represent further external components in this meaning in addition to the mobile device 14 and the cloud 17.

The connection to both the furniture part 14 and also the service center 18 or the building technology 19 take place in this case directly from the analyzing unit 9'. It is alternatively or additionally conceivable that data is predominantly transmitted from the analyzing unit 9' via the direct data connection 15 into the cloud 17. Both the service center and also the mobile device 14 and the building technology 19 can alternatively acquire the data from the cloud 17, which corresponds to an indirect data transmission 15' with respect to the analyzing unit 9'. In this case, as explained in greater detail hereafter, individual access rights to specific items of the data can be assigned to the specific data recipients.

The service center 18 is used for checking the technical functionality of the analyzing unit 9' and optionally a control unit 9 of an electric motor furniture drive connected to the analyzing unit 9' or to the bed 1. As previously mentioned, the analyzing unit 9' can also be integrated into such a control unit 9 or can be connected thereto.

The control unit 9 can also be considered to be an external component, with which the analyzing unit 9' exchanges data. In particular, it can receive items of information via the analyzing unit 9' about the present operating state of the electric motor furniture drive and also store them in the form of time series and, for example, relay them to the cloud 17. It is also possible to add such time series which relate to the electric motor furniture drive to the data 25.

The service center 18 can, in particular upon a reclamation request of a user of the system, access data stored in the analyzing unit 9' and/or in the cloud 17, which contain information about the functionality of the analyzing unit 9', connected sensors 12, or components of the electric motor furniture drive. This also includes, for example, items of information about the data 25, for example, whether and for which days the data 25 are provided. To protect the privacy of the user, in contrast, certain content of the data 25 themselves, in particular the time series 26-19 of the physiological parameters P stored in the data 25, are not provided to the service center 18. Furthermore, the service center 18 is capable of performing a function check, an error analysis, a software test, a software update, or the like in the bed 1 and the control unit 9 and/or analyzing unit 9' thereof. On the basis of such measures and the remote diagnosis, it is possible without a service technician to remedy or preclude possible faults. Furthermore, it is possible to be able to locate a fault in greater detail, so that a service technician can provide his/her targeted service.

In principle, an online connection between the bed 1 and the service center 18 is provided in the scope of a remote diagnosis. It can be expedient in this case if the service center 18 has a restricted access to the control unit 9 and to the analyzing unit 9'. The service center 18 has the option of being able to retrieve all items of information about the regular operation of the analyzing unit 9' and/or the control unit 9. Functional diagnoses can thus be carried out. Furthermore, it is expedient if the service center 18 can carry out function tests, by way of control commands for executing actions being transmitted to the analyzing unit 9' and/or the control unit 9. For safety reasons, this can only take place in the presence and with authorization of the user and/or the person 16 in direct proximity to the bed 1. As the authorization or security query or security condition, the user or the person 16 can actuate a button on the bed 1, on the control unit 9, on the analyzing unit 9', and/or on the mobile device 14 or a manual operation unit, which is connected to the control unit 9. Alternatively, the security query or authorization can take place by the transmission of the telephone number of the mobile device 14, if the person 16 is listed in the registration database of the service center 18.

The term execution of actions also includes the resetting, calibration, or adjustment of sensors 12 and/or the analyzing unit 9'. Therefore, influences on measured or detected values of the respective sensor 12 because of a mechanical wear of the bed 1 may be compensated for.

A comprehensive function test of all hardware and software of the bed 1 is also possible remotely in the simplest and most convenient manner, as well as being able to perform an adjustment or calibration of the at least one sensor 12 and/or the analyzing unit 9'.

In a further embodiment, the mobile device 14 is used as a communication connection device like a modem. A communication connection device, referred to in short hereafter as a modem, establishes the connection between bed 1, control unit 9, and/or analyzing unit 9' on one side and the mobile radio network on the other side. It is therefore possible in the simplest manner to be able to establish the connection between the bed 1, the control unit 9, and/or the analyzing unit 9' with the service center 18. Ideally, the bed 1, the control unit 9, and/or the analyzing unit 9' communicates via a first radio transmission link with the mobile device 14. The first transmission link is designed as a Bluetooth transmission link or as a WLAN transmission link. The second transmission link is also designed as a radio transmission link and is provided for coupling via the mobile radio network with the Internet.

In the regular operating state, the exchange of data and items of information between the first and the second transmission link is deactivated and can exclusively be activated by the person 16 to make contact with a service center 18. A password query, or the input of a serial number, for example, the serial number of the control unit 9, can be useful for activating the data and information exchange. Furthermore, an encryption of the second transmission link and/or an encryption of the data and items of information to be transmitted can be provided. A maximum of operational security is provided for the person 16 on the basis of these security measures.

If no mobile radio network is provided, in place thereof, a telephone network or a WLAN network or a LAN network can be used, wherein the first and second transmission links mentioned at the outset are adapted to the respective periphery and can be designed as wired transmission links. It is thus possible in the simplest case that the control unit 9 and/or the analyzing unit 9' has a telephone connection and the transmission links mentioned at the outset are coincident with a transmission link in wired form. Alternatively, it is also provided that the first transmission link is formed as a LAN transmission link (local area network) or furthermore alternatively as a WLAN transmission link (wireless local area network).

The building technology 19 is typically understood as a system which can detect and/or control a status of at least electrical (for example, light, alarm system), mechanical (windows, roller blinds), or thermal (heating, air conditioning system) installations. The data connection 15 between the analyzing unit 9' and the building technology 19 enables items of information relevant to one or the other side to be able to be exchanged, and therefore an increased value to be provided for the user of the system. For example, items of information of the analyzing unit which relate to a present sleep state can be relayed to the building technology 19, for example, to open or close roller blinds and/or windows automatically via the building technology 19, to turn a room light on or off, or to activate or deactivate an alarm system installed in the building both globally and also alternatively selectively for only specific rooms, for example, all rooms with the exception of the bedroom. Getting up from the bed 1 during the night can be detected, for example, by the analyzing unit 9' and relayed to the building technology 19, to automatically turn on a hallway light, for example, for a visit to the toilet. Furthermore, the alarm systems of the building can be selectively deactivated in this case.

The analyzing unit 9' recognizes that the respective person has gotten up from the bed 1, because specific or all signals of the at least one sensor 12 are absent. For this purpose, it can be advantageous to provide further sensors 12. A force-sensitive sensor 12 can be useful as the further sensor 12. Because specific signals of sensors 12 change or are no longer present, the analyzing unit 9' computes the logical conclusion, that the respective person has gotten up from the bed. The analyzing unit 9' then outputs a signal to initiate actions, for example, switching on lights in the form of underbed lights or the hallway light mentioned at the outset. The execution of the actions of switching the underbed light takes place by way of the control unit 9. The execution of the action of switching the hallway light takes place by way of the building technology 19. The execution of each action can also be event-oriented, for example, as a function of the time of day or the brightness. Finally, the emission and transfer of items of information corresponding to the status of the respective person 16 in or not in the bed 1 is performed by the analyzing unit 9'.

Any type of logical conclusions or items of information can be emitted by the analyzing unit 9' and/or by the control unit 9 along a wired or wireless transmission link. These items of information are received, for example, by the building technology 19 or by a mobile device 14.

The detection of whether a person 16 is located in the bed or not can be used in manifold ways. It is therefore very helpful, for example, for an in-home caregiver if they are made aware of the state of the person 16 in bed and receive the information about this via one of the mentioned transmission links.

In addition, it can also be very helpful for hotel personnel or their work preparations to know whether a person 16 is still located in the bed or not. Therefore, targeted waking services or room services can be designed. An access to a communication infrastructure, for example, a telephone network, can also take place via the building technology 19, so that an automatic call can optionally be made if specific and worrying physiological states are recognized by the analyzing unit 9'.

Items of information about a room climate and/or an environmental climate (weather, daylight) are frequently also detected by the building technology 19. The analyzing unit 9' can also accept such items of information and buffer them, for example, again in the form of time series and store them in a longer term, possibly as part of the data 25 or separately therefrom in the cloud 17. Such data can subsequently be used in more complex comparative studies to discover interfering influences on the sleep behavior of the user of the system. Data of the building technology 19 can be linked, for example, to various sleep phases or a change between the sleep phases.

In addition to the detection, storage, analysis, and display of physiological parameters and transformation thereof to further computed results in the form of a sleep quality value, other parameters of the surroundings relating to the detection, storage, and analysis can therefore also be used to be able to determine the sleep quality value even more specifically. This is because parameters perceived as particularly physiologically unpleasant, for example, an excessively warm, cold, or bright environment during the resting phase, impair the sleep quality.

It is therefore alternatively provided that these environment-related parameters such as temperature, ambient humidity, background noise, brightness, or the like are detected and analyzed separately from and in parallel to the physiological parameters. These can also be described as environmental quality values and can be stored as a time series in the cloud 17. The person 16 is therefore capable of being able to compare a sleep quality value as a function of an environmental quality value and be able to draw his/her own inferences therefrom. The person 16 is thus given the option being able to define and determine the refinements for improving their own sleep themselves and also recognize the refinements themselves. For example, the person 16 can define the optimum environmental temperature, the optimum ambient humidity, etc., themselves, and also the respective inclination adjustment of individual support surfaces of the mattress or the bed 1. Such items of information on the inclination or adjustment height of individual support surfaces of the bed 1 also offer, as bed-specific parameters, important input variables for defining and establishing an optimum sleep and can also be stored in time series and in a cloud 17.

Environment-related parameters can be provided by the building technology 19. The manner of the provision and the transmission and communication between the analyzing unit 9', the control unit 9, and the building technology 19 is illustrated in greater detail by FIG. 8.

Bed-specific parameters can be provided by the control unit 9 and/or the analyzing unit 9' and transmitted in data form thereto, and can also be part of the data 25 stored in the cloud 17 as an information value or as a time series.

Figure 7:
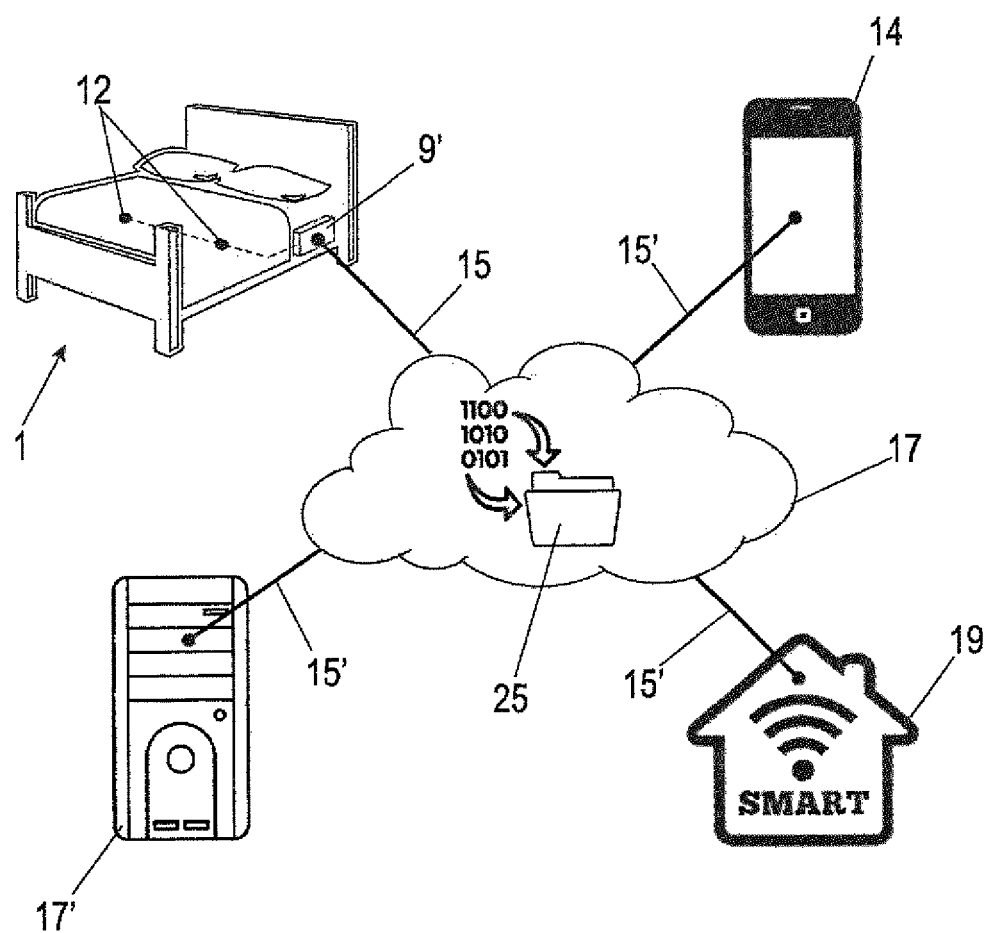

FIG. 7 shows a further exemplary embodiment of a system comparable to that shown in FIGS. 5 and 6. Reference is again made to the description of FIGS. 5 and 6. In contrast to, for example, the system of FIG. 6, in that of FIG. 7, a data transmission from the analyzing unit 9' directly only to the cloud 17 is provided. Further devices such as the mobile device 14 and the building technology 19 access the data 25 stored in the cloud 17 or further data stored therein in the manner of the indirect data transmission 15', wherein access restrictions to only specific parts of the data can again be provided. In an alternative embodiment, the access of a service center to the data stored in the cloud 17 can additionally be provided.

A computer service 17' has further access to the data 25 in the cloud in the illustrated exemplary embodiment. The computer service 17' indicates that further processing and analysis of the data within the cloud 17 can take place by a computer service, which is provided in conjunction with the cloud 17.

Figure 8:
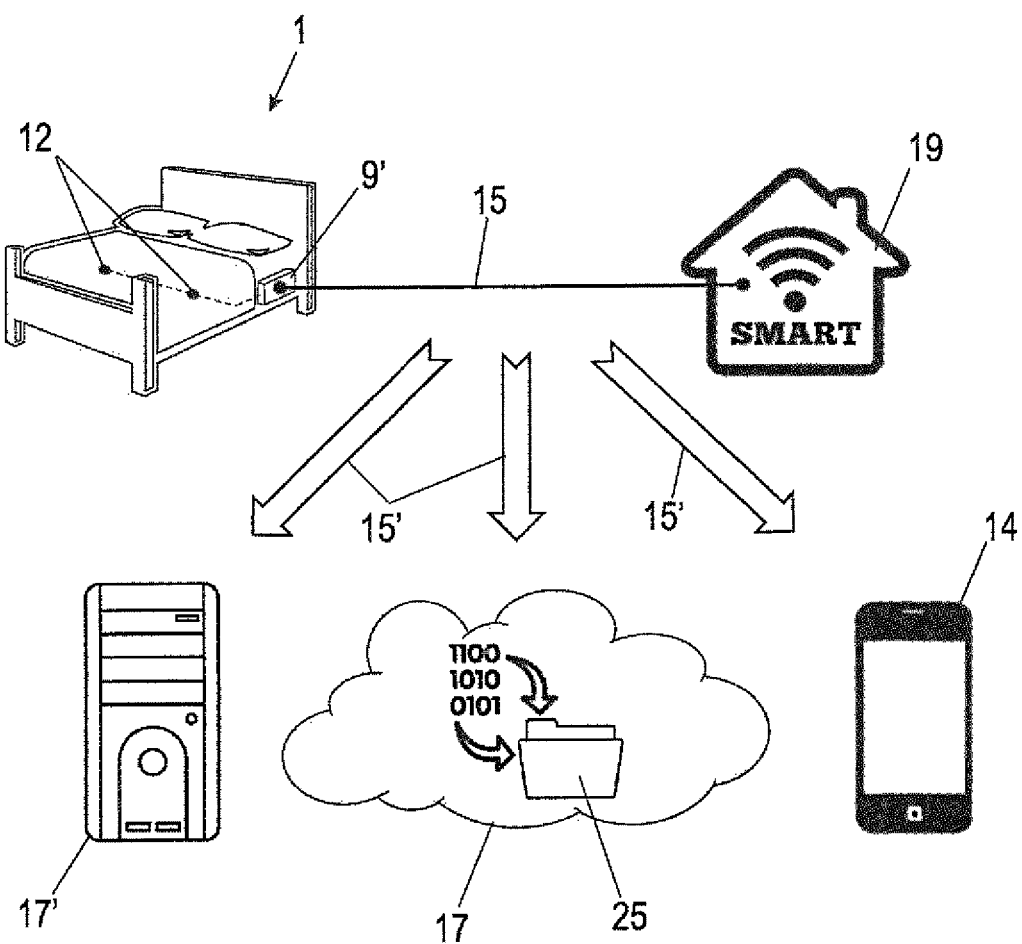

FIG. 8 shows a further system for detecting physiological parameters in the same manner as FIGS. 5 to 7. Reference is again made to the statement on the preceding exemplary embodiments. In contrast to the previous examples, in this example, the connection between the analyzing unit 9' and the building technology 19 is in the foreground. There is only a direct data connection between these two. In addition, the data detected by the analyzing unit 9' and/or the building technology 19 are tapped via indirect data connections 15' and transmitted to the cloud 17, the computer service 17' connected thereto, and/or the mobile device 14.

The data transmissions 15, 15' described in conjunction with FIGS. 1 to 8 run inside a network. The network can have standardized and/or proprietary interfaces and transmission links. While the direct data connection according to the example according to FIG. 8 is of a proprietary nature, other data transmissions 15' are designed by means of standardized transmission links or interfaces, for example, as LAN, WLAN, Bluetooth, or ZigBee.

If it is necessary for data to be transmitted from one interface or transmission link to another, modems or signal converters can be used, so that, for example, a Bluetooth device such as the mobile device 14 can exchange its data with a ZigBee device.

Since the bed 1 with its components such as the control unit 9 or the analyzing unit 9' is also part of such a network, it is possible to provide data between the analyzing unit 9', the building technology 1, the mobile device 14, further devices of an apartment such as television and multimedia devices in bundled form to a number of control programs. The respective control program is executable in the respective device.

A first control program of the building technology 19 is thus conceivable, which recognizes a behavior pattern of the person 16 as a function of the time of day and classifies it as a procedure "going to bed". A transmission of items of information then takes place to the control unit 9 of the bed 1, wherein a mattress heater (not shown in greater detail) is turned on by the control unit 9. The heating of the mattress can moreover take place as a function of the room temperature. The room temperature can be measured in this case by a sensor which is associated with the building technology 19. A value of the room temperature can be transmitted via the data transmissions 15' to the control unit 9 for the analyzing unit 9'.

Another control program of the control unit 9 and/or the analyzing unit 9' detects the presence of the person 16 in the bed with the aid of the signal of the respective sensors 12 as described in greater detail at the outset. Furthermore, sleeping aids in the form of routines and subprograms can be provided, wherein the respective subprogram is controlled as a function of the respective sleep phase. A first subprogram can keep the light slightly dimmed. A further subprogram can control a special light program having comforting color progressions. A further subprogram can cause the emission of relaxing melodies or of sleeping music. A further subprogram, which is started for a sleep phase of the regular sleep, can turn off the ambient light and/or the further sleeping aids or even also multimedia devices such as televisions.

The above-mentioned bed 1 is to be understood in the meaning of this application and invention as sleeping and reclining furniture and is to be mentioned by way of example for all types of sleeping and reclining furniture. Other embodiments of sleeping and reclining furniture are recliners or sofas. In particular, recliners have at least one movable back part, one movable leg part, and one seat part arranged between the back part and the leg part, wherein the movable parts can be moved by the user into a nearly recumbent and sleep-like position, because of which the analogy to a bed 1 is given. This also applies to sofas, in which at least the back part may be moved such that the sofa is used as sleeping or reclining furniture.

The invention claimed is:

1. An analyzing unit for connection to a sensor, which can be coupled to a sleeping or reclining furniture to detect vibration, movement, and/or sound, said analyzing unit being configured
to process and analyze a signal generated by the sensor, to detect a physiological parameter of a person using the sleeping or reclining furniture, and
to transmit data reflective of the detected physiological parameter to an external component, said external component being a component of a building automation system, wherein items of information of the analyzing unit which relate to a present sleep state are relayed to the component of the building automation system to control at least electrical, mechanical, or thermal installations.

2. The analyzing unit of claim 1, configured to transmit the data to or to exchange the data with an external mass storage unit.

3. The analyzing unit of claim 2, wherein the external mass storage unit is a cloud.

4. The analyzing unit of claim 1, further configured to exchange the data with the component of the building automation system.

5. The analyzing unit of claim 1, configured to transmit the data to or to exchange the data with a control unit of an electric motor furniture drive.

6. The analyzing unit of claim 5, constructed for integration into the control unit of the electric motor furniture drive.

7. The analyzing unit of claim 1, configured to transmit the data to or to exchange the data with a mobile device.

8. The analyzing unit of claim 1, comprising a filter, in particular a lowpass filter or a bandpass filter, for signal processing.

9. The analyzing unit of claim 1, comprising a storage unit for buffering a time curve of the physiological parameter.

10. The analyzing unit of claim 1, comprising a transmission unit for a wireless data transmission, in particular via a WLAN or Bluetooth transmission link.

11. A method for analyzing signals of a sensor, which is coupled to sleeping or reclining furniture to detect vibration, movement, and/or sound, said method comprising:
detecting sensor data generated by the sensor at a first repetition frequency;
analyzing the sensor data in a local analyzing unit and ascertaining a physiological parameter at a second repetition frequency, which is less than the first repetition frequency; and
transmitting the ascertained physiological parameter to an external component which is further remote from the sensor than the analyzing unit.

12. The method of claim 11, wherein the detected physiological parameter is a heart rate, a respiratory rate, a movement behavior, and/or a snoring behavior of at least one person.

13. The method of claim 11, wherein the physiological parameter is buffered in the local analyzing unit in the form of time curves, before being transferred to the external component.

14. The method of claim 13, further comprising:
extracting in a sleeping period sleep states and time proportions of the sleep states from the time curves in the local analyzing unit; and
transmitting the sleep states and the time proportions of the sleep states to the external component.

15. A sleeping or reclining furniture, in particular a bed, comprising:
a sensor configured to detect vibration, movement, and/or sound; and
an analyzing unit connected to the sensor and configured to process and analyze a signal generated by the sensor, to detect a physiological parameter of a person using the sleeping or reclining furniture, and to transmit data reflective of the detected physiological parameter to an external component, said sleeping or reclining furniture being configured to execute a method as set forth in claim 11.

16. The sleeping or reclining furniture of claim 15, wherein the analyzing unit is configured to transmit the data to or to exchange the data with an external mass storage unit as the external component.

17. The sleeping or reclining furniture of claim 16, wherein the external mass storage unit is a cloud.

18. The sleeping or reclining furniture of claim 15, wherein the analyzing unit is configured to transmit the data to or to exchange the data with a component of a building automation system.

19. The sleeping or reclining furniture of claim 15, wherein the analyzing unit is configured to transmit the data to or to exchange the data with a control unit of an electric motor furniture drive.

20. The sleeping or reclining furniture of claim 19, wherein the analyzing unit is constructed for integration into the control unit of the electric motor furniture drive.

21. The sleeping or reclining furniture of claim 15, wherein the analyzing unit is configured to transmit the data to or to exchange the data with a mobile device.

22. The sleeping or reclining furniture of claim 15, wherein the analyzing unit comprises a filter for signal processing, in particular a low-pass filter or a bandpass filter.

23. The sleeping or reclining furniture of claim 15, wherein the analyzing unit comprises a storage unit for buffering a time curve of the physiological parameter.

24. The sleeping or reclining furniture of claim 15, wherein the analyzing unit comprises a transmission unit for a wireless data transmission, in particular via a WLAN or Bluetooth transmission link.

\* \* \* \* \*